United States Patent
Kitazawa

(10) Patent No.: US 9,109,985 B2
(45) Date of Patent: Aug. 18, 2015

(54) MALFUNCTION DETECTING DEVICE AND MALFUNCTION DETECTING METHOD FOR COOLING DEVICE

(75) Inventor: Osamu Kitazawa, Okazaki (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 14/347,184

(22) PCT Filed: Sep. 27, 2011

(86) PCT No.: PCT/JP2011/071974
§ 371 (c)(1),
(2), (4) Date: Mar. 25, 2014

(87) PCT Pub. No.: WO2013/046309
PCT Pub. Date: Apr. 4, 2013

(65) Prior Publication Data
US 2014/0233602 A1    Aug. 21, 2014

(51) Int. Cl.
*G01K 3/00* (2006.01)
*G01K 1/14* (2006.01)
*G01K 13/00* (2006.01)
*G01K 7/00* (2006.01)
*G01N 11/00* (2006.01)
(Continued)

(52) U.S. Cl.
CPC *G01N 11/00* (2013.01); *B60K 1/00* (2013.01); *B60L 3/00* (2013.01); *H01L 23/473* (2013.01); *H02P 29/0088* (2013.01); *B60K 11/02* (2013.01); *B60K 11/04* (2013.01); *B60K 2001/003* (2013.01); *B60K 2001/006* (2013.01); *G01N 2011/0093* (2013.01); *H01L 2924/0002* (2013.01); *H02M 2001/327* (2013.01)

(58) Field of Classification Search
CPC .. H01L 23/472; H01L 23/46; H05K 7/20927; H05K 7/20218; H01K 7/20254
USPC ............................ 374/141, 112, 145, 165, 45
See application file for complete search history.

(56) References Cited

U.S. PATENT DOCUMENTS 5,959,351 A * 9/1999 Sasaki et al. .................. 257/714
7,683,582 B2 * 3/2010 Zhu et al. ...................... 320/150
(Continued)

FOREIGN PATENT DOCUMENTS

JP          7-146188 A    6/1995
JP      H 08-250882 A    9/1996
(Continued)

OTHER PUBLICATIONS

International Search Report of PCT/JP2011/071974, dated Dec. 20, 2011.

*Primary Examiner* — Mirellys Jagan
(74) *Attorney, Agent, or Firm* — Sughrue Mion, PLLC

(57) ABSTRACT

An ECU executes a program including the steps of: obtaining a first temperature Ta of a first semiconductor element; obtaining a second temperature Tb of a third semiconductor element; determining that it is in a normal state in which clogging has not occurred, when a rotating speed Nm2 of a second MG is more than a threshold value Nm2 and the magnitude of a difference between the first temperature Ta and the second temperature Tb is less than a threshold value ΔT; and determining that the clogging of a foreign matter has occurred in a predetermined site when the magnitude of the difference between the first temperature Ta and the second temperature Tb is equal to or more than the threshold value ΔT.

5 Claims, 5 Drawing Sheets

(51) Int. Cl.
  *B60L 3/00* (2006.01)
  *H01L 23/473* (2006.01)
  *H02P 29/00* (2006.01)
  *B60K 1/00* (2006.01)
  *H02M 1/32* (2007.01)
  *B60K 11/02* (2006.01)
  *B60K 11/04* (2006.01)

(56) References Cited

U.S. PATENT DOCUMENTS

2006/0225867 A1 10/2006 Park et al.
2008/0290506 A1 11/2008 Aoki et al.
2010/0067560 A1* 3/2010 Kouda et al. .................. 374/145
2010/0254081 A1* 10/2010 Koenig et al. ............ 361/679.46

FOREIGN PATENT DOCUMENTS

| JP | 2006-294978 A | 10/2006 |
| JP | 2006-295178 A | 10/2006 |
| JP | 2008-256313 A | 10/2008 |
| JP | 2008-294069 A | 12/2008 |
| JP | 2009-171702 A | 7/2009 |
| JP | 2009-277053 A | 11/2009 |

* cited by examiner

MALFUNCTION DETECTING DEVICE AND MALFUNCTION DETECTING METHOD FOR COOLING DEVICE

CROSS REFERENCE TO RELATED APPLICATIONS

This application is a National Stage of International Application No. PCT/JP2011/071974 filed Sep. 27, 2011, the contents of all of which are incorporated herein by reference in their entirety.

TECHNICAL FIELD

The present invention relates to malfunction detection for a cooling device for cooling an electric device including a plurality of semiconductor elements.

BACKGROUND ART

A vehicle having a motor as a driving source, such as a hybrid vehicle or an electric vehicle, is provided with an electric device including semiconductor elements, such as an inverter. Further, such a vehicle is provided with a cooling device that employs coolant for cooling the electric device.

As a technique to detect a malfunction in such a cooling device, for example, Japanese Patent Laying-Open No. 2006-294978 (PTD 1) discloses a technique to detect a malfunction in a cooling device based on a temperature of an electric device including semiconductor elements and a temperature of coolant.

CITATION LIST

Patent Document

PTD 1: Japanese Patent Laying-Open No. 2006-294978

SUMMARY OF INVENTION

Technical Problem

If a malfunction occurs in the cooling device, it is desirable to specify the fault location. However, the above-described patent publication does not disclose at all to specify the fault location when the malfunction occurs in the cooling device. Accordingly, for example, a fault location resulting from clogging of a foreign matter in a passage for the coolant in the cooling device cannot be distinguished from a fault location resulting from failure of other component(s).

The present invention has an object to provide a malfunction detecting device and a malfunction detecting method for a cooling device for cooling an electric device including a plurality of semiconductor elements, so as to specify a fault location when a malfunction occurs in the cooling device.

Solution to Problem

A malfunction detecting device according to a certain aspect of the present invention is a malfunction detecting device for a cooling device for cooling an electric device provided in a vehicle and including a first semiconductor element and a second semiconductor element. Substantially a same magnitude of currents flow in the first semiconductor element and the second semiconductor element. The cooling device includes a first heat dissipating portion for dissipating heat of the first semiconductor element, a second heat dissipating portion for dissipating heat of the second semiconductor element, and a coolant passage for allowing coolant to flow in the first heat dissipating portion and the second heat dissipating portion in parallel. The coolant passage is provided with a predetermined site which is formed in advance and in which clogging of a foreign matter is likely to occur on a path via which the coolant flows into the first heat dissipating portion. The malfunction detecting device includes: a first temperature detecting unit for detecting a first temperature of the first semiconductor element; and a control unit for detecting occurrence of the clogging in the predetermined site when a magnitude of a difference between the first temperature and a second temperature of the second semiconductor element exceeds a permissible value.

Preferably, the control unit estimates the second temperature using at least one of the current flowing in the second switching element, an operating frequency of the second switching element, and a temperature of the coolant.

More preferably, the malfunction detecting device further includes a second temperature detecting unit for detecting the second temperature.

More preferably, the first heat dissipating portion and the second heat dissipating portion are disposed in parallel with each other and are formed integrally to be a heat exchanger having a plate-like shape. The heat exchanger has an inlet connected to the coolant passage such that the coolant flows from an inlet of the second heat dissipating portion to an inlet of the first heat dissipating portion. The predetermined site is formed at an end portion of the inlet of the heat exchanger at a side of the first heat dissipating portion by forming the coolant passage such that the coolant passage has a cross sectional area decreasing as the coolant passage extends from the inlet of the second heat dissipating portion to the inlet of the first heat dissipating portion.

A malfunction detecting method according to another aspect of the present invention is a malfunction detecting method for a cooling device for cooling an electric device including a first semiconductor element and a second semiconductor element. Substantially a same magnitude of currents flow in the first semiconductor element and the second semiconductor element. The cooling device includes a first heat dissipating portion for dissipating heat of the first semiconductor element, a second heat dissipating portion for dissipating heat of the second semiconductor element, and a coolant passage for allowing coolant to flow in the first heat dissipating portion and the second heat dissipating portion in parallel. The coolant passage is provided with a predetermined site which is formed in advance and in which clogging of a foreign matter is likely to occur on a path via which the coolant flows into the first heat dissipating portion. The malfunction detecting method includes the steps of: detecting a first temperature of the first semiconductor element; and detecting occurrence of the clogging in the predetermined site when a magnitude of a difference between the first temperature and a second temperature of the second semiconductor element exceeds a permissible value.

Advantageous Effects of Invention

According to the present invention, the predetermined site in which the clogging of the foreign matter is likely to occur is formed on the flow path of the cooling water that cools the first semiconductor element. In this way, the occurrence of the clogging in the predetermined site can be detected when the temperature difference between the first semiconductor element and the second semiconductor element, in which substantially the same magnitude of current flows, exceeds the permissible value. Accordingly, a malfunction detecting device and a malfunction detecting method for a cooling device for cooling an electric device including a plurality of semiconductor elements can be provided to specify a fault location when a malfunction occurs in the cooling device.

DESCRIPTION OF EMBODIMENTS

Figure 1:
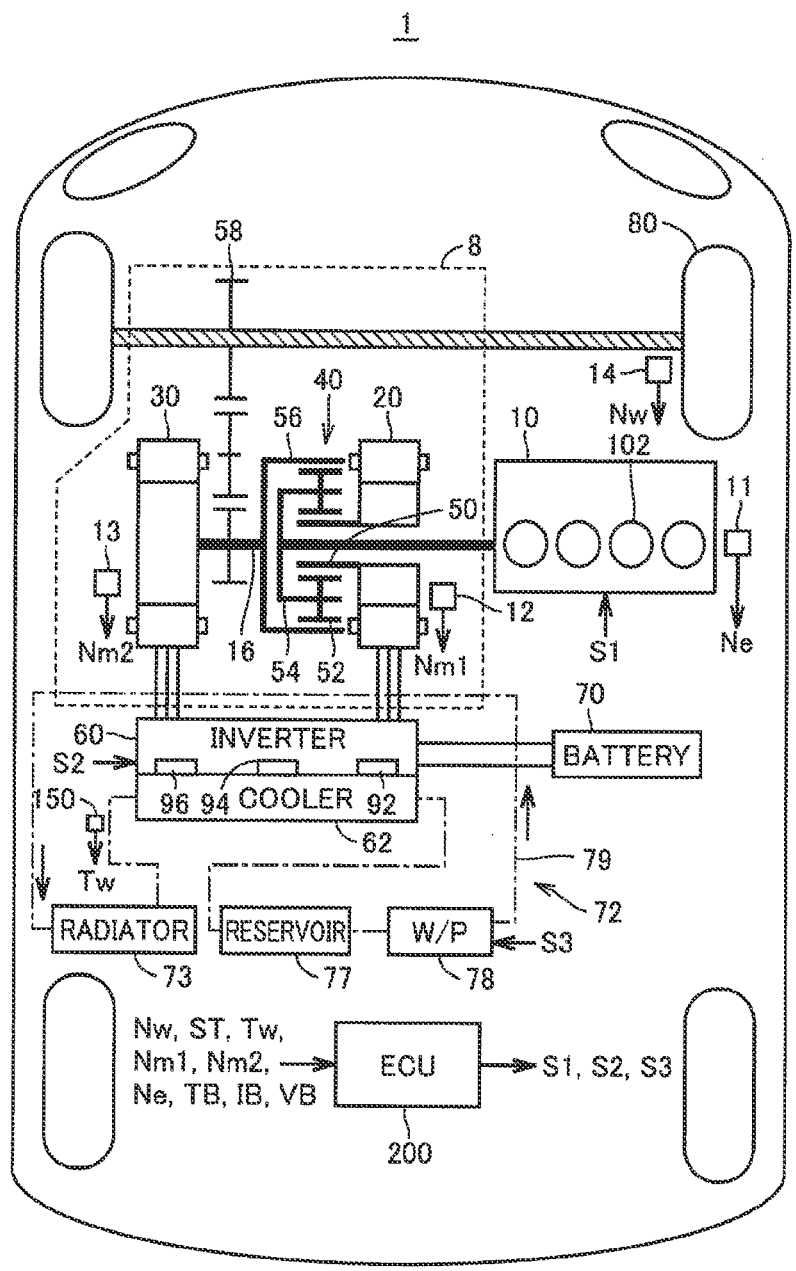
FIG. 1 is an entire block diagram of a vehicle in a first embodiment.

In the following, embodiments of the present invention will be described with reference to figures. In the following description, the same components are denoted with the same reference characters. Their designations and functions are also the same. Therefore, a detailed description thereof will not be repeated.

First Embodiment

Referring to FIG. 1, an entire block diagram of a vehicle 1 according to the present embodiment will be described. Vehicle 1 includes a transmission 8, an engine 10, a wheel speed sensor 14, an inverter 60, a battery 70, a cooling device 72, driving wheels 80, and an ECU (Electronic Control Unit) 200.

Transmission 8 includes a first resolver 12, a second resolver 13, a drive shaft 16, a first motor generator (hereinafter, referred to as "first MG") 20, a second motor generator (hereinafter, referred to as "second MG") 30, a power split device 40, and a speed reducer 58.

This vehicle 1 travels using driving power output from at least one of engine 10 and second MG 30. The driving power generated by engine 10 is split for two paths by power split device 40. One of the two paths is a path via which the driving power is transmitted to driving wheels 80 via speed reducer 58. The other path is a path via which the driving power is transmitted to first MG 20.

Each of first MG 20 and second MG 30 is, for example, a three-phase AC rotating electrical machine. First MG 20 and second MG 30 are driven by inverter 60.

First MG 20 has a function as a generator that generates electric power using the driving power supplied from engine 10 and split by power split device 40, so as to charge battery 70 via inverter 60. Further, first MG 20 receives electric power from battery 70 and rotates a crankshaft, which is the output shaft of engine 10. In this way, first MG 20 has a function as a starter that starts engine 10.

Second MG 30 has a function as a driving motor that provides driving power to driving wheels 80 using at least one of the electric power stored in battery 70 and the electric power generated by first MG 20. Further, second MG 30 has a function as a generator for charging battery 70 via inverter 60 using electric power generated through regenerative braking.

Examples of engine 10 include internal combustion engines such as a gasoline engine and a diesel engine. Engine 10 includes: a plurality of cylinders 102; and a fuel injecting device 104 that supplies fuel to each of the plurality of cylinders 102. Based on a control signal S1 from ECU 200, fuel injecting device 104 injects an appropriate amount of fuel to each cylinder at an appropriate time or stops injecting the fuel to each cylinder.

Further, engine 10 is provided with an engine speed sensor 11 for detecting rotating speed (hereinafter, referred to as "engine speed") Ne of the crankshaft of engine 10. Engine speed sensor 11 sends a signal, which indicates detected engine speed Ne, to ECU 200.

Power split device 40 mechanically couples the following three elements to one another: drive shaft 16 for rotating driving wheels 80; the output shaft of engine 10; and the rotating shaft of first MG 20. Power split device 40 employs one of the above-described three elements as a reaction force element, whereby driving power can be transmitted between the other two elements. The rotating shaft of second MG 30 is coupled to drive shaft 16.

Power split device 40 is a planetary gear mechanism including a sun gear 50, a pinion gear 52, a carrier 54, and a ring gear 56. Pinion gear 52 is engaged with each of sun gear 50 and ring gear 56. Carrier 54 rotatably supports pinion gear 52, and is coupled to the crankshaft of engine 10. Sun gear 50 is coupled to the rotating shaft of first MG 20. Ring gear 56 is coupled to the rotating shaft of second MG 30 and speed reducer 58 via drive shaft 16.

Speed reducer 58 transmits the driving power from power split device 40 and second MG 30 to driving wheels 80. Further, speed reducer 58 transmits reaction force, received by driving wheels 80 from a road surface, to power split device 40 and second MG 30.

Inverter 60 converts DC power stored in battery 70 into AC power for driving first MG 20 and second MG 30. Inverter 60 is controlled based on a control signal S2 from ECU 200. Inverter 60 converts the DC power of battery 70 into AC power and sends it to first MG 20 and/or second MG 30. In this way, first MG 20 and/or second MG 30 are driven using the electric power stored in battery 70. Further, the inverter converts the AC power, which is generated by first MG 20 and/or second MG 30, into DC power and sends it to battery 70. Accordingly, battery 70 is charged with the electric power generated by first MG 20 and/or second MG 30.

Inverter 60 includes a plurality of semiconductor elements. Each of the semiconductor elements is, for example, a switching element such as an IGBT (Insulated Gate Bipolar Transistor) element. In the present embodiment, inverter 60 includes: a first semiconductor element 92 corresponding to the U phase; a second semiconductor element 94 corresponding to the V phase; and a third semiconductor element 96 corresponding to the W phase. Currents having different phases and substantially the same magnitude flow in first semiconductor element 92, second semiconductor element 94, and third semiconductor element 96. Inverter 60 includes: a group of semiconductor elements, which correspond to the three phases, for driving first MG 20; and a group of semiconductor elements, which correspond to the three phases, for driving second MG 30. In the description below, it is assumed that first semiconductor element 92, second semiconductor element 94, and third semiconductor element 96 are the group of semiconductor elements, which correspond to the three phases, for driving second MG 30.

Battery 70 is a power storage device, and is a rechargeable DC power source. Examples of battery 70 include secondary batteries such as a nickel hydride battery and a lithium ion battery. The voltage of battery 70 is, for example, about 200 V. Battery 70 may be charged with the electric power generated by first MG 20 and/or second MG 30 as described above, and may be charged with electric power supplied from an external power source (not shown). It should be noted that battery 70 is not limited to the secondary battery and may be any battery capable of outputting DC voltage, such as a capacitor, a solar cell, or a fuel cell.

First resolver 12 detects rotating speed Nm1 of first MG 20. First resolver 12 sends a signal indicating detected rotating speed Nm1 to ECU 200. Second resolver 13 detects rotating speed Nm2 of second MG 30. Second resolver 13 sends a signal indicating detected rotating speed Nm2 to ECU 200.

Wheel speed sensor 14 detects rotating speed Nw of driving wheels 80. Wheel speed sensor 14 sends a signal indicating detected rotating speed Nw to ECU 200. Based on rotating speed Nw received, ECU 200 calculates a vehicle speed V. It should be noted that instead of rotating speed Nw, ECU 200 may calculate a vehicle speed V based on rotating speed Nm2 of second MG 30.

Cooling device 72 cools inverter 60 as well as first MG 20 and second MG 30 in transmission 8. Cooling device 72 may cool a converter (not shown) in addition to first MG 20, second MG 30, and inverter 60. Cooling device 72 includes a cooler 62, a radiator 73, a reservoir 77, a water pump 78, a cooling water passage 79, and a water temperature sensor 150.

Radiator 73, cooler 62, reservoir 77, water pump 78, and transmission 8 are connected to one another in series in the form of a loop by cooling water passage 79.

Reservoir 77 stores cooling water (coolant) such as antifreezing fluid. When the cooling water circulating in cooling water passage 79 becomes insufficient, cooling water passage 79 is replenished with the cooling water stored in reservoir 77.

Water pump 78 is a pump for circulating the cooling water in a direction indicated by arrows shown in FIG. 1. Water pump 78 is electrically driven. Water pump 78 is operated based on a control signal S3 supplied from ECU 200. ECU 200 may operate water pump 78 when receiving an instruction for starting the system of vehicle 1 (for example, operation of IG-ON), for example. It should be noted that engine 10 may be employed as a driving source for water pump 78.

From the coolant passage, radiator 73 receives the cooling water having cooled first MG 20 and second MG 30 in transmission 8, and cools the received cooling water.

Water temperature sensor 150 is provided between cooler 62 and radiator 73 in cooling water passage 79. Water temperature sensor 150 detects a temperature (hereinafter, referred to as "cooling water temperature") Tw of the cooling water in cooling water passage 79. Water temperature sensor 150 sends a signal indicating detected cooling water temperature Tw to ECU 200.

Figure 2:
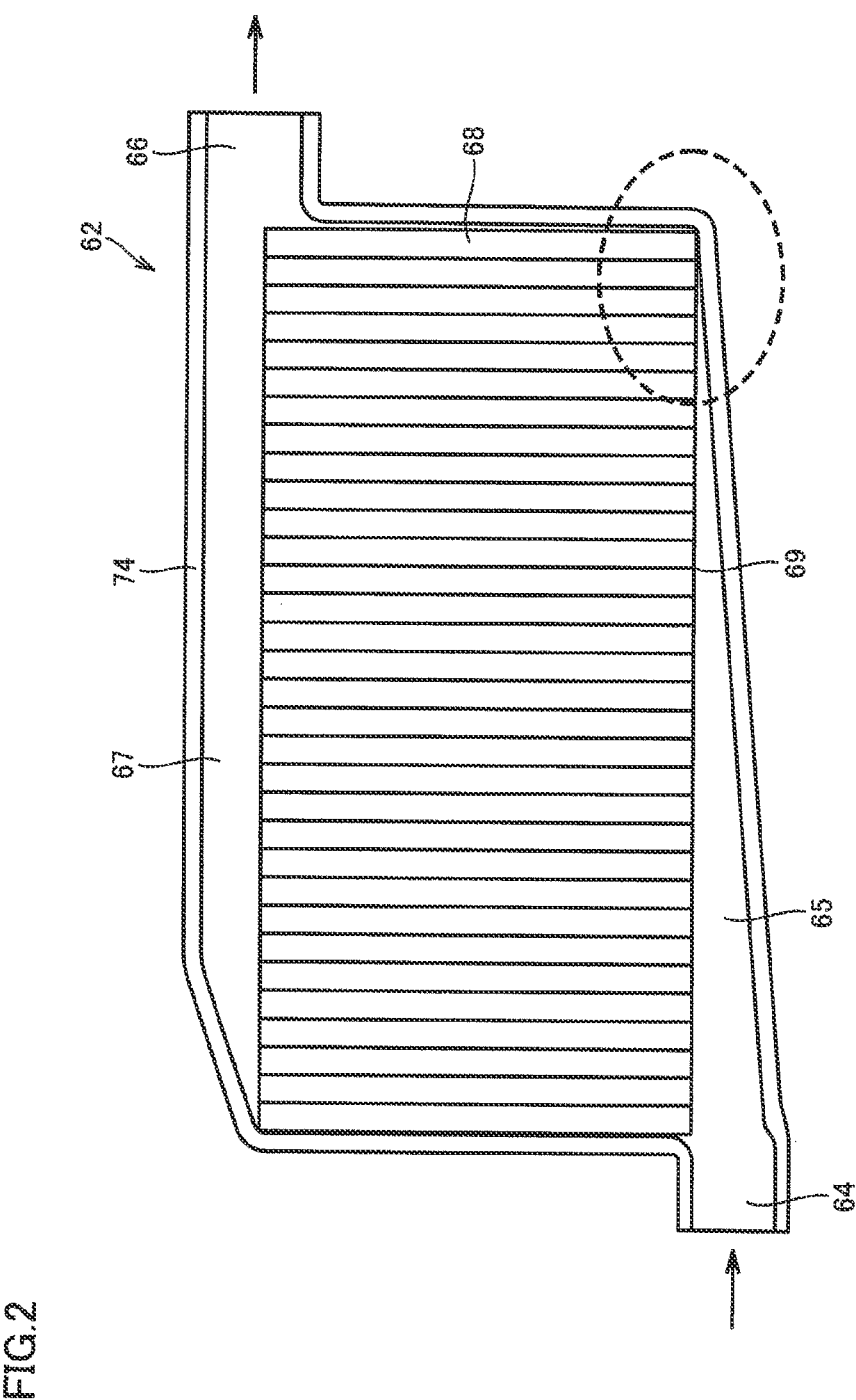
FIG. 2 illustrates a structure of a cooler.

As shown in FIG. 2, cooler 62 includes: an inlet portion 64 for receiving cooling water from radiator 73; an outlet portion 66 for exhausting the cooling water from cooler 62 to reservoir 77; and a cooling fin 68 contained in a housing 74 of cooler 62. Inverter 60, which is an object to be cooled by cooler 62, is provided just above cooling fin 68 in abutment with housing 74.

Figure 3:
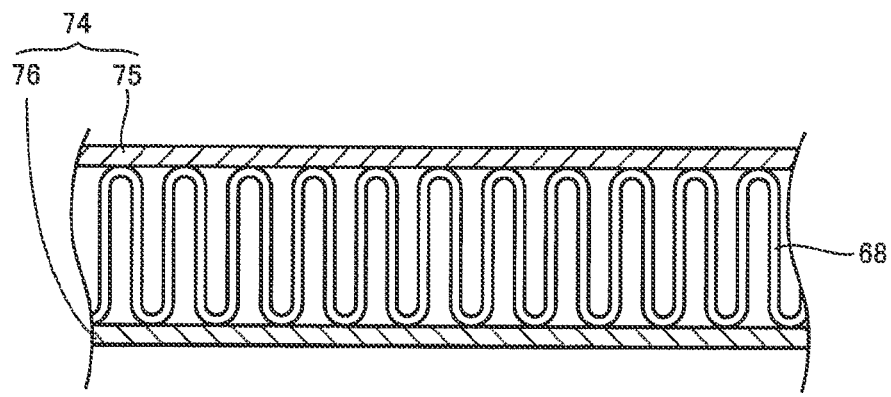
FIG. 3 shows a cross sectional structure of the cooler.

FIG. 3 shows a cross section of a portion of cooling fin 68 of cooler 62. As shown in FIG. 3, cooling fin 68 is in the form of wave in abutment with both of upper surface member 75 of housing 74 and lower surface member 76 of housing 74. It should be noted that each of upper surface member 75 and lower surface member 76 is shaped to have a flat surface having no irregularities. Housing 74 and cooling fin 68 of cooler 62 is formed of, for example, a material having high thermal conductivity, such as aluminum.

The object to be cooled by cooler 62 is provided in abutment with upper surface member 75 and lower surface member 76. Of upper surface member 75 and lower surface member 76, one member in abutment with the object to be cooled may be therefore formed to have a shape having a large contact area with the object to be cooled. Of upper surface member 75 and lower surface member 76, one member not in abutment with the object to be cooled may be alternatively provided with irregularities to increase a surface area exposed to air.

In the present embodiment, it is assumed that upper surface member 75 is provided in abutment with inverter 60, but an object (such as a converter) other than inverter 60 may be provided in abutment with lower surface member 76 for the purpose of cooling.

In addition, in the present embodiment, it is assumed that cooling fin 68 is a member different from housing 74, but instead of cooling fin 68, irregularities (such as irregularities in the form of wave) may be provided such that the one of upper surface member 75 and lower surface member 76 in abutment with the object to be cooled has an increased surface area of its surface in contact with the cooling water, for example.

In the present embodiment, it is assumed that cooling fin 68 is one heat exchanger having heat dissipating portions integrally formed to dissipate heat of each of the plurality of semiconductor elements, but cooling fin 68 is not particularly limited to be constructed of one member. For example, cooling fin 68 may be constructed of a plurality of members.

Referring back to FIG. 2, cooling fin 68 is a heat exchanger formed to have a plate-like shape and have a rectangular plane of projection to upper surface member 75 or lower surface member 76 of housing 74. In cooler 62, a first passage 65 is provided at the inlet portion 64 side relative to cooling fin 68, and a second passage 67 is provided at the outlet portion 66 side relative to cooling fin 68. With water pump 78 being operated, the cooling water having flown from inlet portion 64 flows into first passage 65. The cooling water having flown into first passage 65 passes through cooling fin 68 and then flows into second passage 67. The cooling water having flowing into second passage 67 is exhausted from outlet portion 66.

In the present embodiment, first passage 65 is formed such that the cross sectional area of the passage formed by end portion 69 of cooling fin 68 and housing 74 is decreased as it is further away from inlet portion 64. As shown in FIG. 2, when cooler 62 is taken along a plane parallel to upper surface member 75 or lower surface member 76, first passage 65 has a substantially triangular cross sectional shape having an acute angle such that first passage 65 tapers as it is further away from inlet portion 64. It should be noted that the shape of second passage 67 is not particularly limited.

Figure 4:
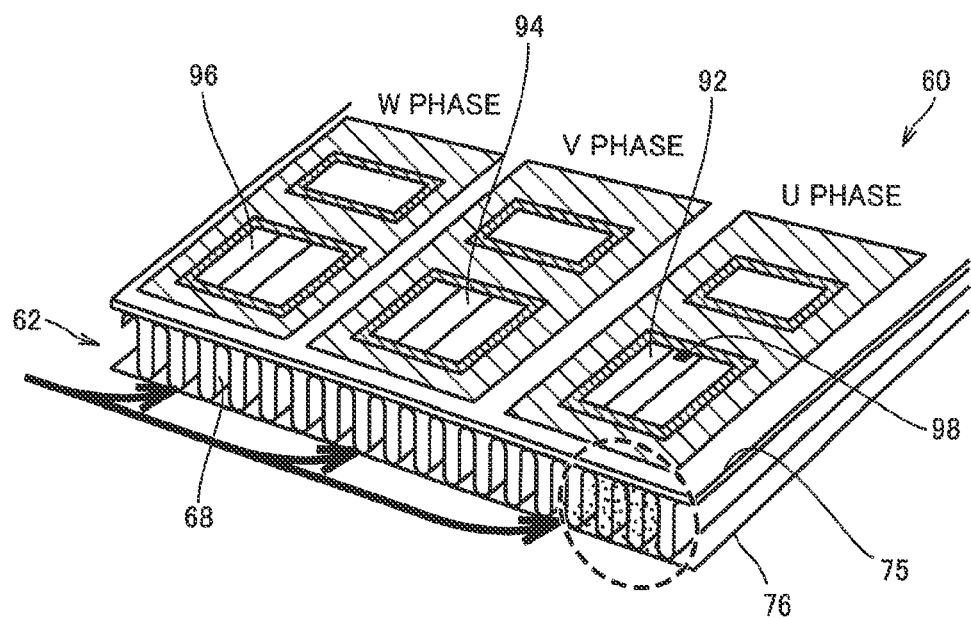
FIG. 4 illustrates configurations of the cooler and an object to be cooled in the first embodiment.

As shown in FIG. 4, first semiconductor element 92, second semiconductor element 94, and third semiconductor element 96 of inverter 60 are provided in abutment with upper surface member 75 of cooler 62. Of first semiconductor element 92, second semiconductor element 94, and third semiconductor element 96, first semiconductor element 92 furthest away from inlet portion 64 is provided with a temperature detecting element 98 in the present embodiment. Temperature detecting element 98 is an element for detecting a first temperature Ta of first semiconductor element 92. Temperature detecting element 98 sends a signal indicating first temperature Ta of first semiconductor element 92 to ECU 200. It should be noted that instead of temperature detecting element 98 provided in first semiconductor element 92, first temperature Ta of first semiconductor element 92 may be detected using a temperature sensor provided separately from first semiconductor element 92.

Further, in the present embodiment, cooler 62 is provided with a predetermined site, which is formed in advance and in which clogging of a foreign matter is likely to occur on a path via which the cooling water flows into a portion of cooling fin 68 just below the location thereof in abutment with first semiconductor element 92. The term "foreign matter" is intended to include, for example, burr produced during manufacturing, a portion of a sealing material, a corrosion product, and the like. In the present embodiment, the predetermined site is formed in a location indicated by a broken line frame in FIG. 2 and FIG. 4. In other words, the predetermined site corresponds to a region that is positioned at an end portion of the inlet of cooling fin 68 away from inlet portion 64 of first passage 65 and that is centered around the portion having the acute angle in the substantially triangular cross section of first passage 65 as shown in FIG. 2. It should be noted that the region of the predetermined site is not limited to the region indicated by the broken line frame shown in FIG. 2 and FIG. 4. Further, with first passage 65 being formed to have the cross section shown in FIG. 2, the flow rate of the cooling water flowing from inlet portion 64 is increased.

ECU 200 generates control signal S1 for controlling engine 10, and sends generated control signal S1 to engine 10. ECU 200 generates control signal S2 for controlling inverter 10, and sends generated control signal S2 to inverter 60.

In order to achieve the most efficient traveling of vehicle 1, ECU 200 controls the entire hybrid system i.e., an charging/discharging state of battery 70 and operating states of engine 10, first MG 20, and second MG 30 by controlling engine 10, inverter 60, and the like.

ECU 200 calculates a requested driving power corresponding to an amount of stepping on an accelerator pedal (not shown) provided in the driver's seat. In accordance with the calculated, requested driving power, ECU 200 controls torques of first MG 20 and second MG 30 and an output of engine 10.

When a malfunction of cooling device 72 occurs in vehicle 1 configured as described above, the clogging of the foreign matter in cooling water passage 79 of cooling device 72 and a fault in another portion (such as water pump 78) are desirably distinguished from each other.

Hence, a feature of the present embodiment lies in that ECU 200 detects the occurrence of the clogging in the above-described predetermined site whenever a difference between first temperature Ta of first semiconductor element 92 and second temperature Tb of third semiconductor element 96 exceeds a permissible value $\Delta T$.

Moreover, in the present embodiment, ECU 200 estimates second temperature Tb using at least one of a current flowing in third semiconductor element 96, an operating frequency of third semiconductor element 96 during a switching operation of third semiconductor element 96, and cooling water temperature Tw.

Further, ECU 200 does not detect the occurrence of the clogging when rotating speed Nm2 of second MG 30, which is driven in accordance with the operations of first semiconductor element 92, second semiconductor element 94, and third semiconductor element 96, is less than a threshold value Nm2(0).

Figure 5:
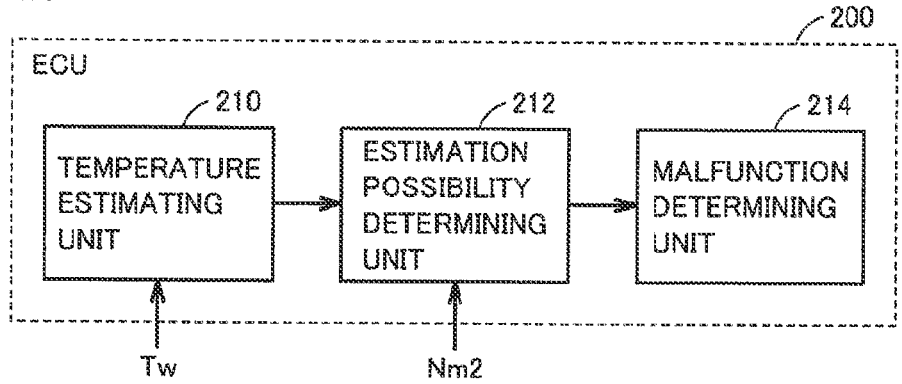
FIG. 5 is a function block diagram of an ECU in the first embodiment.

FIG. 5 shows a function block diagram of ECU 200 provided in vehicle 1 in the present embodiment. ECU 200 includes: a temperature estimating unit 210, an estimation possibility determining unit 212, and a malfunction determining unit 214.

Temperature estimating unit 210 estimates second temperature Tb of third semiconductor element 96. Temperature estimating unit 210 estimates second temperature Tb based on an amount of heat generation and an amount of heat dissipation in third semiconductor element 96. Temperature estimating unit 210 estimates the amount of heat generation based on the current flowing in third semiconductor element 96, the operating frequency thereof during the switching operation, or the like, for example. Further, temperature estimating unit 210 estimates the amount of heat dissipation from third semiconductor element 96 to the cooling water based on cooling water temperature Tw. Temperature estimating unit 210 determines, as an amount of varied heat, an amount of heat obtained by subtracting the amount of heat dissipation from the amount of heat generation, calculates an amount of change in temperature based on the specific heat of third semiconductor element 96, and adds an amount of change previously calculated as the value of second temperature Tb, so as to estimate second temperature Tb of third semiconductor element 96, for example.

Temperature estimating unit 210 may be configured to calculate the amount of change in temperature based on the current flowing in third semiconductor element 96, the operating frequency, cooling water temperature Tw, and a predetermined map, for example. The predetermined map is a map that defines a relation with the current flowing in third semiconductor element 96, the operating frequency, cooling water temperature Tw, and the amount of change in temperature, and is adjusted through experiment or the like.

It should be noted that when starting the operation of inverter 60, temperature estimating unit 210 may set the same value as cooling water temperature Tw for the initial value of second temperature Tb of third semiconductor element 96, for example. Further, the parameters for the estimation of the amount of heat generation or the amount of heat dissipation are not limited to the above-described parameters. For example, the amount of heat dissipation may be corrected based on an amount of operation of water pump 78.

Estimation possibility determining unit 212 determines whether or not third semiconductor element 96 is in a state in which second temperature Tb can be estimated with certain precision. Specifically, estimation possibility determining unit 212 determines whether or not rotating speed Nm2 of second MG 30 is more than threshold value Nm2(0). When rotating speed Nm2 of second MG 30 is more than threshold value Nm2(0), estimation possibility determining unit 212 determines that third semiconductor element 96 is in the state in which second temperature Tb can be estimated with certain precision. For threshold value Nm2(0), a rotating speed is set which has a value of several tens to several hundreds and does not permit lock current flow, for example.

It should be noted that estimation possibility determining unit 212 may bring an estimation possibility determination flag into ON state when rotating speed Nm2 of second MG 30 is more than threshold value Nm2(0), for example.

When estimation possibility determining unit 212 determines that rotating speed Nm2 of second MG 30 is more than threshold value Nm2(0), malfunction determining unit 214 performs a malfunction determining process. For example, when the estimation possibility determination flag is in ON state, malfunction determining unit 214 may perform the malfunction determining process.

Further, malfunction determining unit 214 does not perform the malfunction determining process when estimation possibility determining unit 212 determines that rotating speed Nm2 of second MG 30 is equal to or less than threshold value Nm2(0).

When the magnitude (absolute value) of the difference between first temperature Ta of first semiconductor element 92 detected by temperature detecting element 98 and second temperature Tb of third semiconductor element 96 estimated by temperature estimating unit 210 is less than threshold value ΔT, malfunction determining unit 214 determines that it is in a normal state in which the clogging has not occurred in the predetermined site. It should be noted that threshold value ΔT is set to tolerate a temperature difference resulting from deterioration of at least first semiconductor element 92 or third semiconductor element 96 (set to determine it as the normal state).

On the other hand, when the magnitude of the difference between first temperature Ta and second temperature Tb is equal to or more than threshold value ΔT, malfunction determining unit 214 determines that the clogging has occurred in the predetermined site. For example, when malfunction determining unit 214 determines that the clogging has occurred in the predetermined site, malfunction determining unit 214 may select a predetermined retreat traveling mode to reduce the amount of heat generation (driving power) in inverter 60, or may provide a notification that the clogging has occurred.

In the present embodiment, it is assumed that each of temperature estimating unit 210, estimation possibility determining unit 212, and malfunction determining unit 214 is a component serving as software and implemented by a CPU of ECU 200 executing a program stored in a memory, but they may be implemented by hardware. It should be noted that such a program is recorded in a storage medium and is provided in the vehicle.

Figure 6:
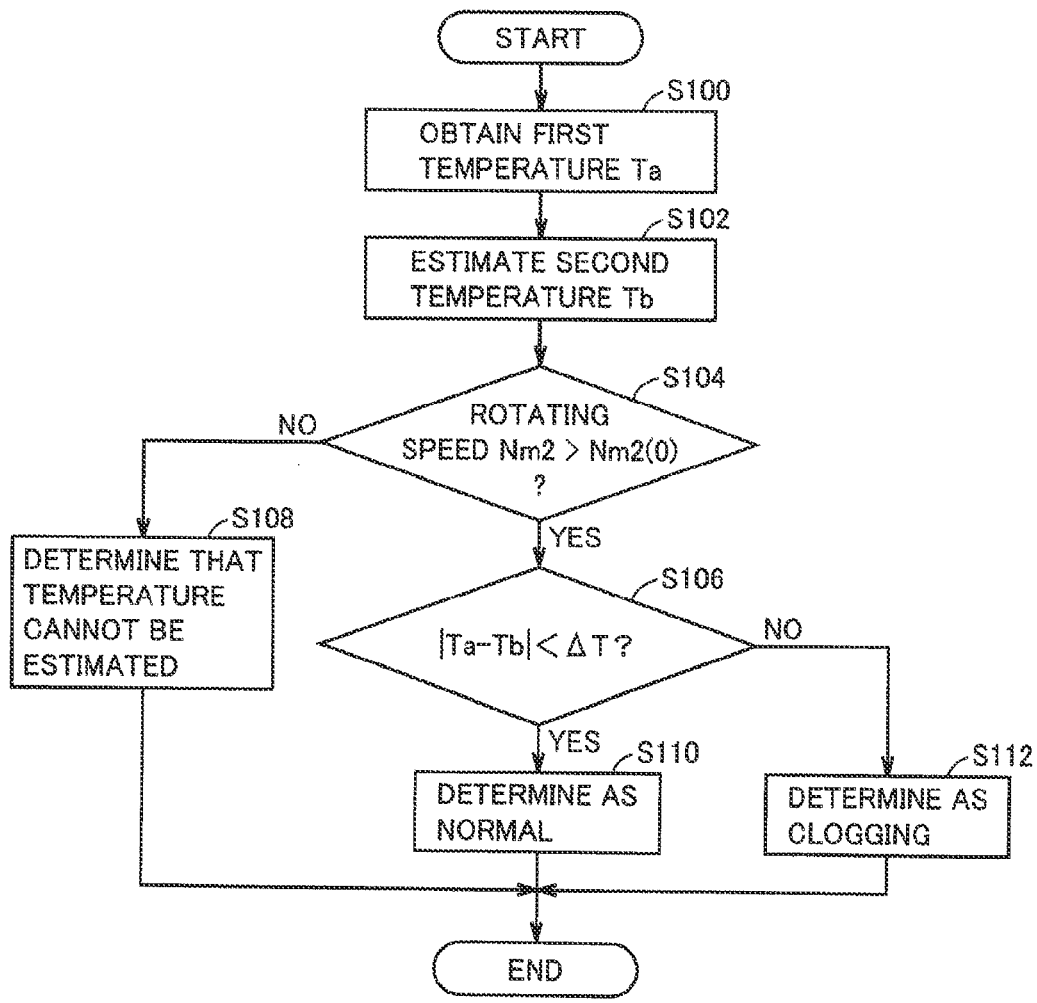
FIG. 6 shows a control structure of a program executed by the ECU in the first embodiment.

Referring to FIG. 6, the following describes a control structure of the program executed by ECU 200 provided in vehicle 1 in the present embodiment.

In a step (hereinafter, the term "step" will be abbreviated as "S") 100, ECU 200 obtains first temperature Ta of first semiconductor element 92 from temperature detecting element 98. In S102, ECU 200 estimates second temperature Tb of third semiconductor element 96.

In S104, ECU 200 determines whether or not rotating speed Nm2 of second MG 30 is more than threshold value Nm2(0). When rotating speed Nm2 of second MG 30 is more than threshold value Nm2(0), the process proceeds to S106. Otherwise (NO in S104), the process proceeds to S108.

In S106, ECU 200 determines whether or not the magnitude of the difference between first temperature Ta of first semiconductor element 92 and second temperature Tb of third semiconductor element 96 is less than threshold value ΔT, which is the permissible value. When the magnitude of the difference between first temperature Ta and second temperature Tb is less than threshold value ΔT (YES in S106), the process proceeds to S110. Otherwise (NO in S106), the process proceeds to S112.

In S108, ECU 200 determines that the temperature of third semiconductor element 96 cannot be estimated, and does not perform the malfunction determining process. In other words, ECU 200 does not perform the detection for the occurrence of the clogging. In S110, ECU 200 determines that it is in the normal state in which the clogging of the foreign matter has not occurred in the predetermined site. In S112, ECU 200 determines that the clogging of the foreign matter has occurred in the predetermined site. In the present embodiment, the malfunction determining process corresponds to the processes of S106, S110, and S112.

The following describes operations of ECU 200 of vehicle 1 in the present embodiment based on the above-described structure and flowchart.

<Case where Rotating Speed Nm2 of Second MG 30 is Low>

In the case where first temperature Ta of first semiconductor element 92 is obtained (S100), second temperature Tb of third semiconductor element 96 is estimated (S102), and rotating speed Nm2 of second MG 30 is equal to or less than threshold value Nm2(0) (NO in S104), it is determined that second temperature Tb cannot be estimated (S108) and the detection for the clogging is not performed.

<Case where Clogging has not Occurred in Predetermined Site>

When first temperature Ta of first semiconductor element 92 is obtained (S100), second temperature Tb of third semiconductor element 96 is estimated (S102), and rotating speed Nm2 of second MG 30 is more than threshold value Nm2(0) (YES in S104), it is determined whether or not the magnitude of the difference between first temperature Ta and second temperature Tb is less than threshold value ΔT (S106).

When no clogging has occurred in the predetermined site, the cooling water having flown from inlet portion 64 to first passage 65 in cooler 62 flows in cooling fin 68 at a substantially uniform flow rate. As a result, the magnitude of the difference between first temperature Ta of first semiconductor element 92 and second temperature Tb of third semiconductor element 96 becomes less than threshold value ΔT (YES in S106). Accordingly, it is determined that it is in the normal state in which the clogging of the foreign matter has not occurred in the predetermined site (S110).

<Case where Clogging has Occurred in Predetermined Site>

In the case where the clogging has occurred in the predetermined site, the flow rate of the cooling water flowing in the portion of cooling fin 68 just below first semiconductor element 92 becomes less than the flow rate of the cooling water flowing in the portion of cooling fin 68 just below third semiconductor element 96. Accordingly, the amount of heat dissipation from first semiconductor element 92 to the cooling water becomes less than the amount of heat dissipation from third semiconductor element 96 to the cooling water. As a result, first temperature Ta of first semiconductor element 92 becomes higher than second temperature Tb of third semiconductor element 96.

When the magnitude of the difference between first temperature Ta and second temperature Tb is equal to or more than threshold value ΔT (NO in S106), it is determined that the clogging of the foreign matter has occurred in the predetermined site (S112).

In this way, according to the malfunction detecting device for the cooling device in the present embodiment, the predetermined site in which the clogging of the foreign matter is likely to occur is formed in cooler 62 on the flow path via which the cooling water flows into the portion of cooling fin 68, which dissipates heat of first semiconductor element 92. When the difference of temperature from that of third semiconductor element 96 in which substantially the same magnitude of current having a different phase flows becomes larger than threshold value ΔT, the occurrence of the clogging in the predetermined site is detected, thereby specifying the fault location of cooling device 72 with high precision. Accordingly, a malfunction detecting device and a malfunction detecting method for a cooling device for cooling an electric device including a plurality of semiconductor elements can be provided to specify a fault location when a malfunction occurs in the cooling device.

Further, when rotating speed Nm2 of second MG 30 is equal to or less than threshold value Nm2(0), the detection for the occurrence of the clogging is not performed, thereby suppressing incorrect detection for the occurrence of the clogging.

In the present embodiment, it has been illustrated that the electric device including the plurality of semiconductor elements and cooled by cooling device 72 is inverter 60, but the converter or the like may be cooled, for example.

In addition, it has been illustrated that the hybrid vehicle shown in FIG. 1 has been described as one example of vehicle 1 to which the present invention is applied, but the vehicle to which the present invention is applied may be any vehicle including an electric device including a plurality of semiconductor elements, and a cooling device for cooling the electric device using coolant. In other words, the vehicle to which the present invention is applied is not particularly limited to the hybrid vehicle shown in FIG. 1, but may be applied to a different type (series type or parallel type) of hybrid vehicle, or may be applied to an electric vehicle or a fuel cell vehicle.

In the present embodiment, the occurrence/non-occurrence of the clogging is determined based on the difference between first temperature Ta of first semiconductor element 92 and second temperature Tb of third semiconductor element 96, but may be determined based on the difference between first temperature Ta of first semiconductor element 92 and the temperature of second semiconductor element 94, for example. It is preferable and desirable to compare first temperature Ta of first semiconductor element 92 with the temperature of the semiconductor element in which the same magnitude of current flows and which is not affected by the occurrence of the clogging.

For example, in the case where a plurality of semiconductor elements including first semiconductor element 92 are connected to one another in parallel for the U phase and there is a semiconductor element that is not affected by the occurrence of the clogging among the plurality of semiconductor elements, the occurrence/non-occurrence of the clogging may be determined based on a difference between the temperature of such a semiconductor element and first temperature Ta of first semiconductor element 92.

In the present embodiment, it has been illustrated that the occurrence/non-occurrence of the clogging in cooling device 72 is detected using the group of semiconductor elements for driving second MG 30, but the occurrence/non-occurrence of the clogging in cooling device 72 may be detected using the group of semiconductor elements included in inverter 60 for driving first MG 20, for example. In other words, the clogging may be detected based on a difference between a temperature of a semiconductor element most affected by the occurrence of the clogging among the group of semiconductor elements for driving first MG 20 (semiconductor element in which the temperature is increased the most) and a temperature of a semiconductor element not affected by the occurrence of the clogging (semiconductor in which the temperature is unchanged).

Second Embodiment

The following describes a malfunction detecting device for a cooling device in a second embodiment. A vehicle including the malfunction detecting device for the cooling device in the present embodiment is different in configuration from vehicle 1 including the malfunction detecting device for the cooling device in the foregoing first embodiment, in terms of a temperature detecting element 99, which is provided to detect second temperature Tb of third semiconductor element 96, and operations of ECU 200. The other configurations are the same as those in vehicle 1 including the malfunction detecting device for the cooling device in the foregoing first embodiment. They are given the same reference characters. Their functions are also the same. Therefore, a detailed description thereof will not be repeated.

Figure 7:
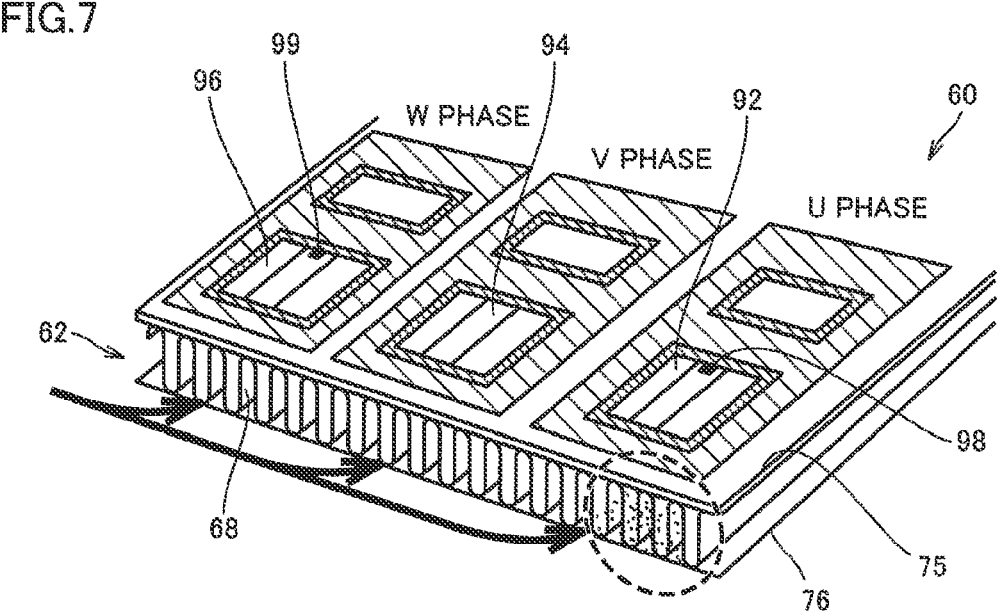
FIG. 7 illustrates configurations of the cooler and an object to be cooled in a second embodiment.

As shown in FIG. 7, in the present embodiment, inverter 60 is provided with a temperature detecting element 99 for detecting second temperature Tb of third semiconductor element 96. It should be noted that the other configuration is the same as the configuration of inverter 60 shown in FIG. 4. Therefore, a detailed description thereof will not be repeated.

A feature of the present embodiment lies in that ECU 200 detects the occurrence of the clogging of the foreign matter in the predetermined site when the magnitude of a difference between first temperature Ta of first semiconductor element 92 detected by temperature detecting element 98 and second temperature Tb of third semiconductor element 96 detected by temperature detecting element 99 exceeds permissible value ΔT.

Figure 8:
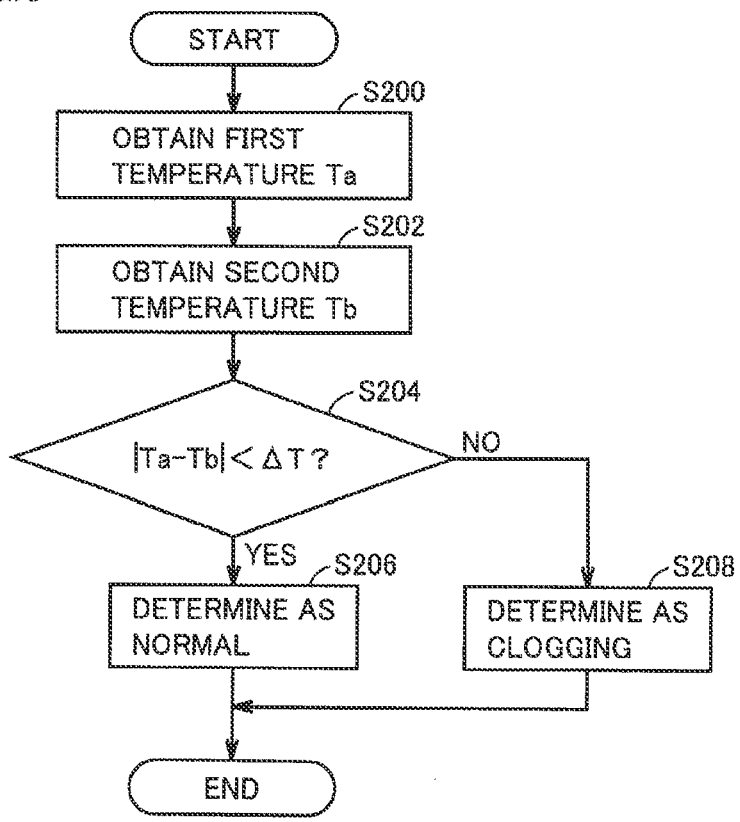
FIG. 8 shows a control structure of a program executed by the ECU in the second embodiment.

Referring to FIG. 8, the following describes a control structure of a program executed by ECU 200 provided in vehicle 1 in the present embodiment.

In S200, ECU 200 obtains first temperature Ta of first semiconductor element 92 from temperature detecting element 98. In S202, ECU 200 obtains second temperature Tb of third semiconductor element 96 from temperature detecting element 99.

In S204, ECU 200 determines whether or not the magnitude of the difference between first temperature Ta of first semiconductor element 92 and second temperature Tb of third semiconductor element 96 is less than threshold value ΔT, which is the permissible value. When the magnitude of the difference between first temperature Ta and second temperature Tb is less than threshold value ΔT (YES in S204), the process proceeds to S206. Otherwise (NO in 204), the process proceeds to S208.

In S206, ECU 200 determines that it is in the normal state in which the clogging of the foreign matter has not occurred in the predetermined site. In S208, ECU 200 determines that the clogging of the foreign matter has occurred in the predetermined site.

The following describes operations of ECU 200 of vehicle 1 in the present embodiment based on the above-described structure and flowchart.

<Case where Clogging has not Occurred in Predetermined Site>

After first temperature Ta of first semiconductor element 92 is obtained (S200) and the second temperature of third semiconductor element 96 is obtained (200), it is determined whether or not the magnitude of the difference between first temperature Ta and second temperature Tb is less than threshold value ΔT (S106).

When the clogging has not occurred in the predetermined site, the cooling water having flown from inlet portion 64 to first passage 65 in cooler 62 flows in cooling fin 68 at a substantially uniform flow rate. As a result, the magnitude of the difference between first temperature Ta of first semiconductor element 92 and second temperature Tb of third semiconductor element 96 becomes less than threshold value ΔT (YES in S204). Accordingly, it is determined that it is in the normal state in which the clogging of the foreign matter has not occurred in the predetermined site (S206).

<Case where Clogging has Occurred in Predetermined Site>

In the case where the clogging has occurred in the predetermined site, the flow rate of the cooling water flowing in the portion of cooling fin 68 just below first semiconductor element 92 becomes less than the flow rate of the cooling water flowing in the portion of cooling fin 68 just below third semiconductor element 96. Accordingly, the amount of heat dissipation from first semiconductor element 92 to the cooling water becomes less than the amount of heat dissipation from third semiconductor element 96 to the cooling water. As a result, first temperature Ta of first semiconductor element 92 becomes higher than second temperature Tb of third semiconductor element 96.

When the magnitude of the difference between first temperature Ta and second temperature Tb is equal to or more than threshold value ΔT (NO in S204), it is determined that the clogging of the foreign matter has occurred in the predetermined site (S208).

In this way, according to the malfunction detecting device for the cooling device in the present embodiment, in addition to the function and effect provided by the malfunction detecting device for the cooling device in the foregoing first embodiment, second temperature Tb of third semiconductor element 96 can be detected using temperature detecting element 99, so that the occurrence/non-occurrence of the clogging can be determined irrespective of rotating speed Nm2 of second MG 30.

The embodiments disclosed herein are illustrative and non-restrictive in any respect. The scope of the present invention is defined by the terms of the claims, rather than the embodiments described above, and is intended to include any modifications within the scope and meaning equivalent to the terms of the claims.

REFERENCE SIGNS LIST

1: vehicle; 8: transmission; 10: engine; 11: engine speed sensor; 12, 13: resolver; 14: wheel speed sensor; 16: drive shaft; 20, 30: MG; 40: power split device; 50: sun gear; 52: pinion gear; 54: carrier; 56: ring gear; 58: speed reducer; 60: inverter; 62: cooler; 64: inlet portion; 65, 67: passage; 66: outlet portion; 68: cooling fin; 69: end portion; 70: battery; 72: cooling device; 73: radiator; 74: housing; 75: upper surface member; 76: lower surface member; 77: reservoir; 78: water pump; 79: cooling water passage; 80: driving wheel; 92, 94, 96: semiconductor element; 98, 99: temperature detecting element; 102: cylinder; 104: fuel injecting device; 150: water temperature sensor; 200: ECU; 210: temperature estimating unit; 212: estimation possibility determining unit; 214: malfunction determining unit.

The invention claimed is:

1. A malfunction detecting device for a cooling device for cooling an electric device provided in a vehicle and including a first semiconductor element and a second semiconductor element, substantially a same magnitude of currents flowing in said first semiconductor element and said second semiconductor element, the cooling device including a first heat dissipating portion for dissipating heat of said first semiconductor element, a second heat dissipating portion for dissipating heat of said second semiconductor element, and a coolant passage for allowing coolant to flow in said first heat dissipating portion and said second heat dissipating portion in parallel, said coolant passage being provided with a predetermined site which is formed in advance and in which clogging of a foreign matter is likely to occur on a path via which said coolant flows into said first heat dissipating portion, the malfunction detecting device comprising:
a first temperature detecting unit for detecting a first temperature of said first semiconductor element; and
a control unit for detecting occurrence of said clogging in said predetermined site when a magnitude of a difference between said first temperature and a second temperature of said second semiconductor element exceeds a permissible value.

2. The malfunction detecting device for the cooling device according to claim 1, wherein said control unit estimates said second temperature using at least one of the current flowing in said second semiconductor element, an operating frequency of said second semiconductor element, and a temperature of said coolant.

3. The malfunction detecting device for the cooling device according to claim 1, further comprising a second temperature detecting unit for detecting said second temperature.

4. The malfunction detecting device for the cooling device according to claim 1, wherein
said first heat dissipating portion and said second heat dissipating portion are disposed in parallel with each other and are formed integrally to be a heat exchanger having a plate-like shape,
said heat exchanger has an inlet connected to said coolant passage such that said coolant flows from an inlet of said second heat dissipating portion to an inlet of said first heat dissipating portion, and
said predetermined site is formed at an end portion of the inlet of said heat exchanger at a side of said first heat dissipating portion by forming said coolant passage such that said coolant passage has a cross sectional area decreasing as said coolant passage extends from the inlet of said second heat dissipating portion to the inlet of said first heat dissipating portion.

5. A malfunction detecting method for a cooling device for cooling an electric device provided in a vehicle and including a first semiconductor element and a second semiconductor element, substantially a same magnitude of currents flowing in said first semiconductor element and said second semiconductor element, the cooling device including a first heat dissipating portion for dissipating heat of said first semiconductor element, a second heat dissipating portion for dissipating heat of said second semiconductor element, and a coolant passage for allowing coolant to flow in said first heat dissipating portion and said second heat dissipating portion in parallel, said coolant passage being provided with a predetermined site which is formed in advance and in which clogging of a foreign matter is likely to occur on a path via which said coolant flows into said first heat dissipating portion, the malfunction detecting method comprising the steps of:
detecting a first temperature of said first semiconductor element; and
detecting occurrence of said clogging in said predetermined site when a magnitude of a difference between said first temperature and a second temperature of said second semiconductor element exceeds a permissible value.

\* \* \* \* \*